(12) United States Patent
Shi et al.

(10) Patent No.: US 10,278,994 B2
(45) Date of Patent: *May 7, 2019

(54) METHOD FOR THE PREPARATION OF SKIPJACK TUNA EXTRACT HAVING URIC ACID-LOWERING EFFECT AND THE USE THEREOF

(71) Applicant: INFINITUS (CHINA) COMPANY LTD., Jiang Men (CN)

(72) Inventors: Bin Shi, Jiang Men (CN); Xiaolei Guo, Jiang Men (CN); Chung Wah Ma, Jiang Men (CN); Ting Zhang, Jiang Men (CN); Wei Zhang, Jiang Men (CN)

(73) Assignee: INFINITUS (CHINA) COMPANY LTD., Jiang Men (CN)

( * ) Notice: Subject to any disclaimer, the term of this patent is extended or adjusted under 35 U.S.C. 154(b) by 395 days.

This patent is subject to a terminal disclaimer.

(21) Appl. No.: 15/141,103

(22) Filed: Apr. 28, 2016

(65) Prior Publication Data

US 2016/0317586 A1 Nov. 3, 2016

(30) Foreign Application Priority Data

Apr. 30, 2015 (CN) .......................... 2015 1 0221993

(51) Int. Cl.
*A61K 35/60* (2006.01)
*A23L 17/00* (2016.01)
*A23L 17/20* (2016.01)

(52) U.S. Cl.
CPC .............. *A61K 35/60* (2013.01); *A23L 17/20* (2016.08); *A23L 17/65* (2016.08); *A23V 2002/00* (2013.01); *A61K 2236/00* (2013.01)

(58) Field of Classification Search
None
See application file for complete search history.

(56) References Cited

FOREIGN PATENT DOCUMENTS

CN 102808010 A * 12/2012

OTHER PUBLICATIONS

U.S. Appl. No. 15/140,925, filed Apr. 2016, Guo; Xiaolei.*

* cited by examiner

*Primary Examiner* — Michael Barker
(74) *Attorney, Agent, or Firm* — Parker Highlander PLLC

(57) ABSTRACT

The present invention discloses a method for the preparation of skipjack tuna extract having hypouricemic effect and the use thereof, which is simple in processing operations, low in production cost, and is free from pollution. The prepared skipjack tuna extract has a potent hypouricemic effect, and has a significant therapeutic effect on hyperuricemia, with no toxic and side effects. The method in an example of the present invention comprises: pretreating skipjack tuna to obtain a skipjack tuna slurry; enzymolysing the skipjack tuna slurry to obtain a crude enzymolysis liquid; removing fishy smell and bitter taste, removing impurities by activated charcoal, and filtering to obtain a refnded enzymolysis liquid; concentrating under vacuum and spray-drying to obtain the skipjack tuna extract. The present invention further discloses use of the skipjack tuna extract in health care products or food products.

2 Claims, 2 Drawing Sheets

METHOD FOR THE PREPARATION OF SKIPJACK TUNA EXTRACT HAVING URIC ACID-LOWERING EFFECT AND THE USE THEREOF

This application claims the benefit of priority to Chinese Patent Application No. 201510221993.X, filed Apr. 30, 2015. The entire content of the above-referenced disclosure is specifically incorporated herein by reference.

FIELD OF THE INVENTION

The present invention relates to the field of health care products, especially relates to a method for the preparation of skipjack tuna extract having uric acid-lowering effect and the use thereof.

BACKGROUND OF THE INVENTION

Hyperuricemia refers to a body state in which the concentration of serum uric acid goes beyond the normal range. It is generally believed that a hyperuricemia should be considered when the serum uric acid concentration ≥416 μmol/L for male and ≥357 μmol/L for female. Hyperuricemia is the most important biochemical basis for gout, and is susceptible to develop gouty arthritis, tophi deposition, and joint deformity. In recent years, it has been reported in literatures at home and abroad that hyperuricemia is associated with the incidence of hypertension, hyperlipidemia, coronary heart disease, stroke, diabetes, etc. Thus, studies on hyperuricemia have attracted clinical attentions.

Currently available drugs for the treatment of hyperuricemia are mainly divided into three major categories: drugs such as allopurinol and febuxostat, both of them have an inhibitory effect on xanthine oxidase, the key enzyme in the production of uric acid; and uricosuric synthetic drugs such as benzbromarone, metyrapone, etc.; and drugs such as rasburicase and PEG-uricase, etc. which promote the decomposition of uric acid. In recent years, some Chinese patent medicines also show uric acid-lowering effects and are commercially available.

However, the compositions of Chinese patent medicines are complex, which show slow effect, indefinite action target, and their uric acid-lowering effect also varies with each individual. Meanwhile, all of the drugs such as allopurinol, febuxostat, benzbromarone, metyrapone, rasburicase, and PEG-uricase, etc. have certain toxic and side effects. They often cause other physical discomforts while achieving the uric acid-lowering purpose, and thereby attend to one thing and lose another, which limits the use of these drugs somehow.

SUMMARY OF THE INVENTION

The present invention provides a method for the preparation of skipjack tuna extract having uric acid-lowering effect, and use thereof in health care product or food product. The skipjack tuna extract of the present invention is simple in processing operations, low in production cost, free from pollution, simple and accurate in in vitro screening indexes, and potent in uric acid-lowering activity. Meanwhile, the skipjack tuna extract of the present invention can significantly reduce the serum creatinine level, and has a certain protective effect on renal function, and is free from toxic and side effects.

The preparation method of the present invention is simple in processing operations, low in production cost, free from pollution, and simple and accurate in in vitro screening indexes.

In addition, the raw materials of the present invention come from skipjack tuna which is readily available. The prepared skipjack tuna extract shows potent uric acid-lowering activity and has significant therapeutic effects against hyperuricemia as verified by animal experiments.

For this reason, the present invention provides a method for the preparation of skipjack tuna extract having uric acid-lowering effect, which can comprise:

(1) removing the head and viscera of the skipjack tuna before mincing, adding 1 to 2 times of water by weight of the minced skipjack tuna meat, heating under stirring within 80 to 100° C. for 5 to 30 min, and then lowering the temperature within 50 to 55° C. to obtain a skipjack tuna slurry;

(2) adding 0.2% to 3.2% of protease by weight of the minced skipjack tuna meat to the skipjack tuna slurry, carrying out hydrolyzation for 5 to 9 h while keeping the temperature within 50 to 55° C., then heating within 85 to 95° C. which is kept for 15 to 30 min to deactivate the enzyme, and centrifuging to obtain a supernatant, which is a crude enzymatic hydrolysate;

(3) adding 0.5% to 1.0% of activated charcoal to the crude enzymatic hydrolysate by weight, stirring for 0.5 to 1.0 hour within a temperature of 45 to 55° C., and then filtering through a 0.5 μm filter paper to obtain a refined enzymatic hydrolysate;

(4) concentrating the refined enzymatic hydrolysate under vacuum and spray-drying to obtain the skipjack tuna extract.

Preferably, the protease consists of one or more of the neutrase, flavourzyme, papain, Alcalase and proteolytic enzyme.

The present invention further provides a skipjack tuna extract having uric acid-lowering effect prepared by the above-described preparation method.

The present invention further provides a health care product or food product containing the above-described skipjack tuna extract.

Preferably, the preparation of the health care product is in the form of oral liquid, capsule, tablet, pill, powder, pulvis, or granule.

The present invention further provides the use of the above-described skipjack tuna extract in health care product or food product.

Preferably, the skipjack tuna extract is comprised in an amount of 0.5% to 70% of the health care product or food product by weight.

In an example of the present invention, the head and viscera of the skipjack tuna are removed, cleaned completely and minced by a meat mincer; 1 to 2 times of water is added to the minced skipjack tuna meat by weight, the resultant mixture is heated under stirring within 80 to 100° C. for 5 to 30 min, and then the temperature is lowered within 50 to 55° C.; 0.6% to 1.2% of neutrase and 1.0 to 2.0% of flavourzyme by weight of the minced skipjack tuna meat are added to the skipjack tuna meat slurry, and hydrolyzation is carried out for 5 to 9 h within a temperature of 50 to 55° C.; then the temperature is increased within 85 to 95° C. and kept for 15 to 30 min to deactivate the enzyme; a supernatant is obtained by centrifugation, to which 0.5% to 1.0% of activated charcoal by weight of the supernatant is added; the resultant mixture is stirred for 0.5 to 1.0 hour within a temperature of 45 to 55° C., then filtered through a 0.5 μm filter paper, and the obtained filtrate is a refined enzymatic hydrolysate, which is concentrated under vacuum and through spray-dried to obtain the skipjack tuna extract.

The skipjack tuna extract was prepared into health care product or food product alone or in combination with other traditional Chinese medicine having uric acid-lowering effect according to conventional preparation technology. The method for the preparation of skipjack tuna extract having uric acid-lowering effect according to the present invention is simple in operation, low in production cost, free from pollution, simple and accurate in in vitro screening indexes. Meanwhile, the active polypeptide ingredients of the skipjack tuna were reserved which has a potent uric acid-lowering activity, and can significantly reduce the serum creatinine level, has certain protective effects on renal function, and is free from toxic and side effects.

In addition, the raw materials of the present invention come from skipjack tuna which is readily available. The prepared skipjack tuna extract shows potent uric acid-lowering activity and has significant therapeutic effects against hyperuricemia as verified by animal experiments.

DETAILED EMBODIMENTS

Figure 1:
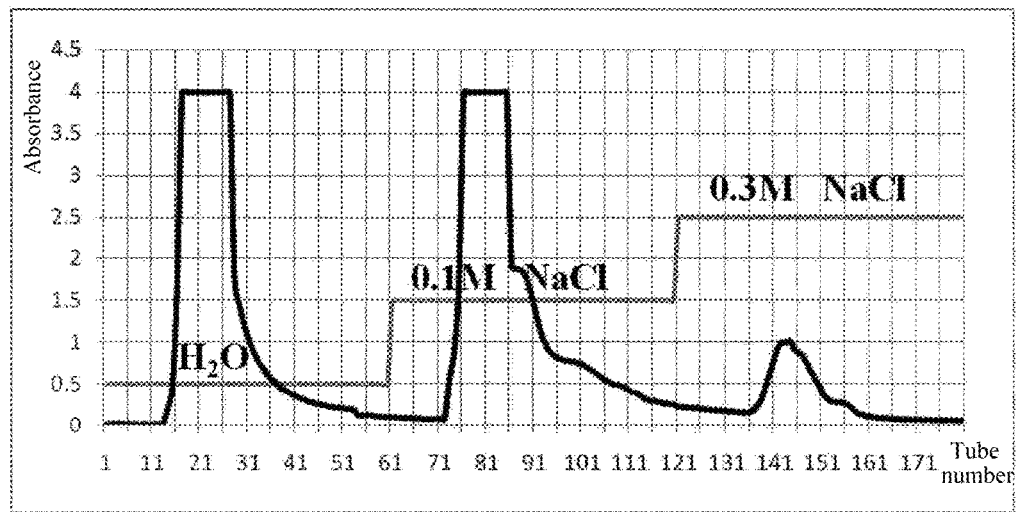
FIG. 1 is the constitutional diagram of the peptide powder of Example 1 after separation by ion-exchange resin.

The examples of the present invention provide a method for the preparation of skipjack tuna extract having uric acid-lowering effect and use thereof, for reducing the content of uric acid.

The present invention provides a method for the preparation of skipjack tuna extract having uric acid-lowering effect: firstly removing and mincing the head and viscera of the skipjack tuna, adding 1 to 2 times of water by weight of the minced skipjack tuna meat, heating under stirring within 80 to 100° C. for 5 to 30 min, then lowering the temperature within 50 to 55° C. to obtain a skipjack tuna slurry; adding 0.2% to 3.2% of protease by weight of the minced skipjack tuna meat to the skipjack tuna slurry, carrying out hydrolyzation for 5 to 9 h while keeping the temperature within 50 to 55° C., then heating up to 85 to 95° C. which is kept for 15 to 30 min to deactivate the enzyme, the supernatant obtained by centrifugation is a crude enzymatic hydrolysate; removing fishy smell and bitter taste: adding 0.5% to 1.0 wt % of activated charcoal to the crude enzymatic hydrolysate, stirring for 0.5 to 1.0 hour within a temperature of 45 to 55° C., filtering through a 0.5 μm filter paper to obtain a refined enzymatic hydrolysate; concentrating the refined enzymatic hydrolysate under vacuum and spray-drying to obtain the skipjack tuna extract; preparing the skipjack tuna extract into a health care product or food product, which can be in the form of oral liquid, capsule, tablet, pill, powder, pulvis, or granule. The skipjack tuna extract can be comprised in an amount of 0.5% to 70% of the health care product or food product by weight.

The method for the preparation of skipjack tuna extract having uric acid-lowering effect according to the present invention is simple in operation, low in production cost, free from pollution, simple and accurate in in vitro screening indexes. Meanwhile, the active polypeptide ingredients of the skipjack tuna were reserved which has a potent uric acid-lowering activity, and can significantly reduce the serum creatinine level, has certain protective effects on renal function, and is free from toxic and side effects. In addition, the raw materials of the present invention come from readily available skipjack tuna. The prepared skipjack tuna extract shows potent uric acid-lowering activity and has significant therapeutic effects against hyperuricemia as verified by animal experiments.

In order to make technicians of this field better understand the technical solutions of the present invention, the present invention is further illustrated in detail through the following specific examples.

EXAMPLE 1

(1) The head and viscera of the skipjack tuna were removed, cleaned completely, and minced by a meat mincer. 500 kg of minced skipjack tuna was weighed, and 500 kg of water was added. The resultant mixture was heated under stirring at 100° C. for 10 min to obtain a skipjack tuna meat slurry. The temperature was then lowered to 50° C.

(2) 5 kg of neutrase and 7.5 kg of flavourzyme were added to the skipjack tuna meat slurry, hydrolyzation was carried out for 5 hours at a temperature kept at 50° C., and then the mixture was heated at 95° C. for 15 min to deactivate the enzyme. Finally, centrifugation was carried out to obtain a supernatant, and a crude enzymatic hydrolysate of skipjack tuna was thus obtained;

(3) 8 kg of activated charcoal was added to the crude enzymatic hydrolysate of skipjack tuna. The resultant mixture was stirred for 1.0 hour at a temperature kept at 50° C., then filtered through a 0.5 μm filter paper, and the obtained filtrate was the refined enzymatic hydrolysate of the skipjack tuna.

(4) The refined enzymatic hydrolysate of skipjack tuna was concentrated under vacuum to obtain solid matter with a content of 30%, which was then spray-dried to obtain 50 kg of skipjack tuna extract peptide powder A.

Figure 2:
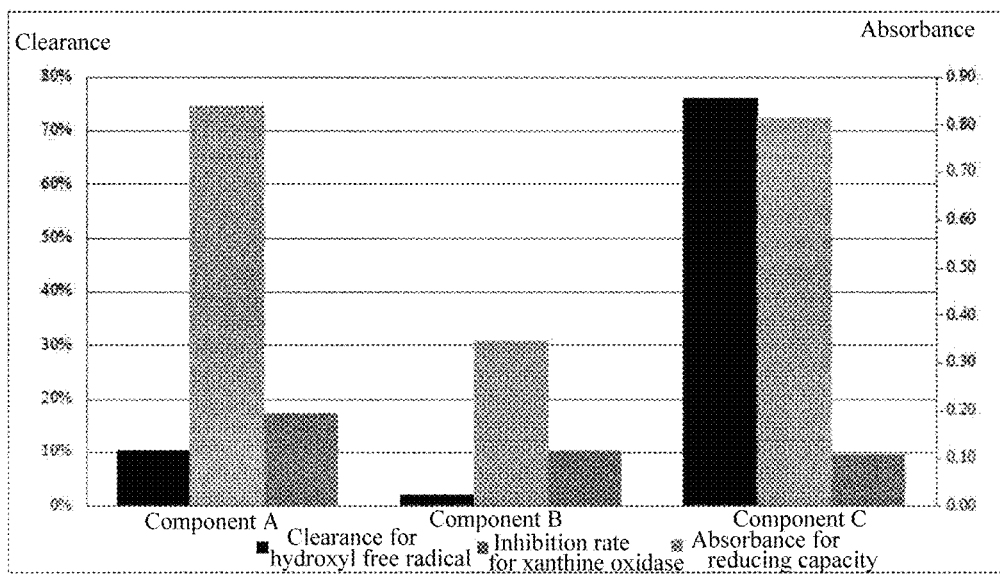
FIG. 2 shows the analysis of inhibitory activity of each component of the peptide powder of Example 1 on xanthine oxidase, and the antioxidant activity thereof
Figure 3:
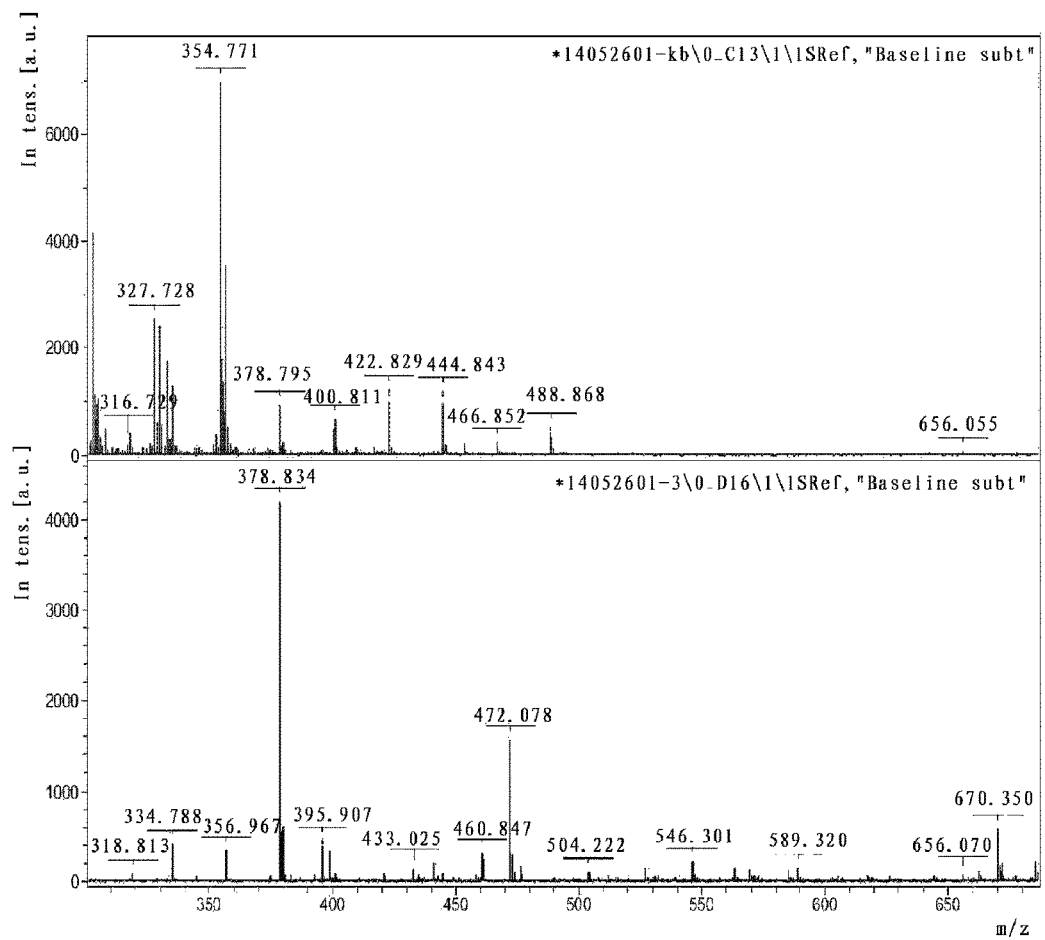
FIG. 3 is the MALDI-TOF-MS primary mass spectrogram of the peptide powder of Example 1.

FIG. 1 is the constitutional diagram of the peptide powder A after separation by ion-exchange resin. FIG. 2 shows the analysis of the inhibitory activity of each component of the peptide powder A on xanthine oxidase, and the antioxidant activity thereof. FIG. 3 is the MALDI-TOF-MS primary mass spectrogram of the peptide powder A. As is shown in FIG. 3, the molecular weight of the main effective peptide components of the peptide powder A was determined to be less than 5000 Da by MALDI-TOF-MS mass spectrometry.

EXAMPLE 2

(1) The head and viscera of the skipjack tuna were removed, cleaned completely, and minced by a meat mincer. 500 kg of minced skipjack tuna was weighed, and 1000 kg of water was added. The resultant mixture was heated under stirring at 100° C. for 10 min to obtain a skipjack tuna meat slurry. The temperature was then lowered to 50° C.

(2) 7.5 kg of papain was added to the skipjack tuna meat slurry, hydrolyzation was carried out for 5 hours at a temperature kept at 50° C., and then the mixture was heated at 95° C. for 15 min to deactivate the enzyme. Finally, centrifugation was carried out to obtain a supernatant, and a crude enzymatic hydrolysate of skipjack tuna was thus obtained;

(3) 8 kg of activated charcoal was added to the crude enzymatic hydrolysate of skipjack tuna. The resultant mixture was stirred for 1.0 hour at a temperature kept at 50° C., then filtered through a 0.5 μm filter paper, and the obtained filtrate was the refined enzymatic hydrolysate of the skipjack tuna.

(4) The refined enzymatic hydrolysate of skipjack tuna was concentrated under vacuum to obtain solid matter with a content of 30%, which was then spray-dried to obtain 40 kg of skipjack tuna extract peptide powder B.

The molecular weight of the main effective peptide components was determined by MALDI-TOF-MS mass spectrometry to be less than 1000 Da.

EXAMPLE 3

(1) The head and viscera of the skipjack tuna were removed, cleaned completely, and minced by a meat mincer. 500 kg of minced skipjack tuna was weighed, and 500 kg of water was added. The resultant mixture was heated under stirring at 100° C. for 10 min to obtain a skipjack tuna meat slurry. The temperature was then lowered to 50° C.

(2) 7.5 kg of alcalase was added to the skipjack tuna meat slurry, hydrolyzation was carried out for 5 hours at a temperature kept at 50° C., and then the mixture was heated at 95° C. for 15 min to deactivate the enzyme. Finally, centrifugation was carried out to obtain a supernatant, and a crude enzymatic hydrolysate of skipjack tuna was thus obtained;

(3) 8 kg of activated charcoal was added to the crude enzymatic hydrolysate of skipjack tuna. The resultant mixture was stirred for 1.0 hour at a temperature kept at 50° C., then filtered through a 0.5 μm filter paper, and the obtained filtrate was the refined enzymatic hydrolysate of skipjack tuna.

(4) The refined enzymatic hydrolysate of skipjack tuna was concentrated under vacuum to obtain solid matter with a content of 30%, which was then spray-dried to obtain 60 kg of skipjack tuna extract peptide powder C.

The molecular weight of the main effective peptide components was determined by MALDI-TOF-MS mass spectrometry to be less than 1000 Da.

EXAMPLE 4

(1) The head and viscera of the skipjack tuna were removed, cleaned completely, and minced by a meat mincer. 500 kg of minced skipjack tuna was weighed, and 500 kg of water was added. The resultant mixture was heated under stirring at 100° C. for 10 min to obtain a skipjack tuna meat slurry. The temperature was then lowered to 50° C.

(2) 2.5 kg of Alcalase and 5 kg of hydrolysis protease were added to the skipjack tuna meat slurry, hydrolyzation was carried out for 5 hours at a temperature of 50° C., and then the mixture was heated at 95° C. for 15 min to deactivate the enzyme. Finally, centrifugation was carried out to obtain a supernatant, and a crude enzymatic hydrolysate of skipjack tuna was thus obtained;

(3) 8 kg of activated charcoal was added to the crude enzymatic hydrolysate of skipjack tuna. The resultant mixture was stirred for 1.0 hour at a temperature kept at 50° C., then filtered through a 0.5 μm filter paper, and the obtained filtrate was the refined enzymatic hydrolysate of the skipjack tuna.

(4) The refined enzymatic hydrolysate of the skipjack tuna was concentrated under vacuum to obtain solid matter with a content of 30%, which was then spray-dried to obtain 60 kg of skipjack tuna extract peptide powder D.

The molecular weight of the main effective peptide components was determined by MALDI-TOF-MS mass spectrometry to be less than 5000 Da.

EXAMPLE 5

(1) The head and viscera of the skipjack tuna were removed, cleaned completely, and minced by a meat mincer. 500 kg of minced skipjack tuna was weighed, and 700 kg of water was added. The resultant mixture was heated under stirring at 80° C. for 30 min to obtain a skipjack tuna meat slurry. The temperature was then lowered to 60° C.

(2) 1.0 kg of Alcalase were added to the skipjack tuna meat slurry, hydrolyzation was carried out for 9 hours at a temperature of 55° C., and then the mixture was heated at 85° C. for 30 min to deactivate the enzyme. Finally, centrifugation was carried out to obtain a supernatant, and a crude enzymatic hydrolysate of skipjack tuna was thus obtained;

(3) 6 kg of activated charcoal was added to the crude enzymatic hydrolysate of skipjack tuna. The resultant mixture was stirred for 1.0 hour at a temperature kept at 45° C., then filtered through a 0.5 μm filter paper, and the obtained filtrate was the refined enzymatic hydrolysate of the skipjack tuna.

(4) The refined enzymatic hydrolysate of the skipjack tuna was concentrated under vacuum to obtain solid matter with a content of 30%, which was then spray-dried to obtain 55 kg of skipjack tuna extract peptide powder E.

EXAMPLE 6

(1) The head and viscera of the skipjack tuna were removed, cleaned completely, and minced by a meat mincer. 500 kg of minced skipjack tuna was weighed, and 1000 kg of water was added. The resultant mixture was heated under stirring at 90° C. for 15 min to obtain a skipjack tuna meat slurry. The temperature was then lowered to 55° C.

(2) 6 kg of Alcalase and 10 kg of hydrolysis protease were added to the skipjack tuna meat slurry, hydrolyzation was carried out for 6 hours at a temperature of 50° C., and then the mixture was heated at 90° C. for 20 min to deactivate the enzyme. Finally, centrifugation was carried out to obtain a supernatant, and a crude enzymatic hydrolysate of skipjack tuna was thus obtained;

(3) 15 kg of activated charcoal was added to the crude enzymatic hydrolysate of skipjack tuna. The resultant mixture was stirred for 0.5 hour at a temperature kept at 55° C., then filtered through a 0.5 μm filter paper, and the obtained filtrate was the refined enzymatic hydrolysate of the skipjack tuna.

(4) The refined enzymatic hydrolysate of the skipjack tuna was concentrated under vacuum to obtain solid matter with a content of 30%, which was then spray-dried to obtain 62 kg of skipjack tuna extract peptide powder F.

The molecular weight of the main effective peptide components was determined by MALDI-TOF-MS mass spectrometry to be less than 5000 Da.

EXAMPLE 7

Proportion of parts by weight: Smilacis Glabrae Rhizoma, 18; Cichorii Herba, 13; *Plantaginis* Herba, 10; Coicis Semen, 17; Pueraria Lobata Radix, 7; Alismatis Rhizoma, 3; the skipjack tuna extract D as described in Example 4, 0.3; with which a health care food product having the uric acid-lowering function was prepared.

Animal tests were conducted using the skipjack tuna extracts A, B, C and D as prepared in the above-described Examples.

Since rats share 90% genes with human beings, rats are globally recognized experimental model in the physiological and disease studies on human bodies. During the experiments for verification of uric acid-lowering effects, due to the presence of uricase in rat body, the uric acid will degrade during the metabolic process. Therefore, in the present animal experiment, rats were intragastricly administered with potassium oxonate everyday to block the effects of uricase in the rats, thus the serum uric acid level of the rat increases, and rats having a uric acid content of greater than 110 umol·$L^{-1}$ were determined to be successful models and were further used for the experiments by intragastric administration.

72 SD rats (SPF grade, male, 200±20 (g)) were provided by Laboratory Animals Centre, Guangzhou University of Chinese Medicine (License Number: SCXK(Yue)2013-0020). Reagents: allopurinol tablets (Guangdong P.D. Pharmaceutical Co., Ltd., Approval Number: National Drug Approval No. H44021368); potassium oxonate (Shandong Zhongke Taidou Chemical Co., Ltd., Batch No. 120901); sodium carboxymethyl cellulose (Shanghai Celluloid Factory, Product Standard No. GB2760); uric acid, urea nitrogen (BUN) assay kit (NanJing Jiancheng Bioengineering Institute, Production batch No. 20140306).

Animal grouping and modeling: the rats in modeling group were intragastricly administered with potassium oxonate for one week (once daily), anaesthetized with 3% pentobarbitol sodium (i.p., 30 mg·$kg^{-1}$), and blood (0.5 ml) was collected from retro-orbital vein plexus and centrifuged at 4° C., 3000 rpm for 15 min. The supernatant sera were taken for determining the content of uric acid. Rats in normal control group were intragastricly administered with equal volume of solvent. Those rats having a uric acid content of greater than 110 μmol·$L^1$ were determined to be successful models. The successfully modeled rats were randomly divided into 6 groups (12 rats/group) according to uric acid contents, including one normal group, one model group (equal volume of distilled water), and four skipjack tuna peptide groups. The skipjack tuna peptide groups were intragastricly administered with skipjack tuna extracts A, B, C and D, respectively, with a volume of 10 ml/kg. The model group was administered with equal volume of distilled water. On 7th and 14th day after treatment with the above-described samples, 50 min after the last administration and anesthetization with 3% pentobarbitol sodium (i.p., 30 mg·$kg^{-1}$), blood (0.5 ml) was collected from retro-orbital vein plexus and the serum uric acid content was determined. On 21st day after treatment, the rats were anaesthetized with 3% pentobarbitol sodium, 5 ml of blood was collected from abdominal aorta, and the serum uric acid content was determined. Serum uric acid assay was carried out according to tungstic acid method, which was performed and determined strictly according to the instructions of the kit. Statistical processing: all the data were expressed in ($\bar{x}$±s) and processed with spss 16.0 statistical software.

The results are shown in Table 1 and Table 2. As is shown in Table 1, there is no significant difference in body weight amongst those groups of rats before and after treatment of the model animal with antigout peptides. Before administration, the body weights of the rats are comparable, and thus the results are comparable.

TABLE 1

Effects of antigout peptides on body weight of rats having hyperuricemia induced by potassium oxonate ($\bar{X}$ ± s)

| Groups | Animal number | Before administration | Treatment 7 d | Treatment 14 d | Treatment 21 d |
|---|---|---|---|---|---|
| Normal group | 12 | 222.2 ± 16.7 | 262.3 ± 20.5 | 291.3 ± 27.6 | 319.2 ± 30.1 |
| Model group | 12 | 230.8 ± 11.7 | 274.3 ± 27.6 | 306.3 ± 23.9 | 324.1 ± 24.5 |
| Group A | 12 | 220.7 ± 14.7 | 270.3 ± 22.2 | 284.0 ± 27.8 | 302.1 ± 44.0 |
| Group B | 12 | 230.8 ± 18.4 | 266.2 ± 16.4 | 299.5 ± 25.5 | 314.3 ± 28.1 |
| Group C | 12 | 221.4 ± 8.3 | 268.9 ± 9.5 | 291.8 ± 14.0 | 301.7 ± 12.2 |
| Group D | 12 | 217.9 ± 14.4 | 276.4 ± 24.5 | 290.2 ± 28.6 | 301.3 ± 31.2 |

TABLE 2

Effects of different treating duration of antigout peptides on serum uric acid content of rats having hyperuricemia induced by potassium oxonate ($\bar{X}$ ± s)

| Groups | Before administration | | Treatment 7 d | | Treatment 14 d | | Treatment 21 d | |
|---|---|---|---|---|---|---|---|---|
| | n | Uric acid value (μmol/L) | n | Uric acid value (μmol/L) | n | Uric acid value (μmol/L) | n | Uric acid value (μmol/L) |
| Normal Group | 12 | 74.9 ± 28.7 | 12 | 75.2 ± 23.2 | 12 | 81.4 ± 21.2 | 12 | 72.7 ± 26.0 |
| Model Group | 12 | 225.8 ± 41.7 | 12 | 216.6 ± 32.1a | 12 | 249.8 ± 40.6a | 12 | 212.0 ± 30.0a |
| Group A | 12 | 211.4 ± 31.0 | 12 | 214.5 ± 47.0f | 12 | 205.4 ± 47.5c | 12 | 205.4 ± 47.5c |
| Group B | 12 | 258.8 ± 49.4 | 12 | 213.3 ± 70.0f | | 204.5 ± 62.1c | 12 | 210.7 ± 27.1f |
| Group C | 12 | 235.2 ± 27.0 | 12 | 166.2 ± 59.8c | 12 | 187.9 ± 34.8e | 12 | 189.8 ± 23.9c |
| Group D | 12 | 201.1 ± 54.1 | 12 | 280.2 ± 40.8e | 12 | 277.6 ± 56.0f | 12 | 157.8 ± 36.7e |

Notes:
as compared to normal control group: ap < 0.01; as compared to model group: ep < 0.01, cp < 0.05, fp < 0.05.

As is shown in Table 2, on 7th, 14th and 21th days after treatment with potassium oxonate, the blood uric acid contents in rats of the model group are significantly higher than those in normal control group ($p<0.01$), which indicates a successful animal modeling.

The hyperuricemic mice were treated with the skipjack tuna extracts. The skipjack tuna extract groups A, B, C and D showed an uric acid-lowering effect ($p<0.05$, $p<0.01$). The uric acid content in group C was reduced from 235.2 μmol/L to 189.8 μmol/L (reduced by 19.3%) and remained stable, indicating the skipjack tuna extract in group C has a stable effects of reducing the uric acid content and inhibiting the increase of uric acid on hyperuricemic rats that induced by potassium oxonate, while group A had certain uric acid-lowering effect only on 14th day. Group D was found to be most effective, as the uric acid content was significantly reduced on 21st day from 201.1 μmol/L to 157.8 μmol/L (the uric acid content was reduced by 21.5%), while the uric acid content in the model group was reduced from 225.8 μmol/L to 212.0 μmol/L (reduced by 6.1%). The data above indicates that the extract of the present invention has a significant uric acid-lowering effect.

The above-described Examples are preferred embodiments of the present invention. However, the embodiments of the present invention are not limited to the above-described Examples. Any other alteration, modification, substitution, combination and simplification without departing from the spirit and principle of the present invention are all equivalent alternatives, and are all included within the protection scope of the present invention.

The peptide powder prepared according to the present invention is capable of reducing the serum uric acid levels, and the effect is the best especially when Alcalase and proteolytic enzyme are used for enzymolysis during the preparation process.

The results show that the skipjack tuna extract prepared according to the method of the present invention has a potent uric acid-lowering effect, a significant therapeutic effect on hyperuricemia, has a certain protective effect on renal function; and is free from toxic and side effects as the extract of the present invention is obtained from an edible raw material, i.e., skipjack tuna.

The invention claimed is:

1. A method for the preparation of skipjack tuna (bonito) extract having uric acid lowering effect, comprising:
    (1) removing the head and entrails of the skipjack tuna before mincing, adding 1 to 2 times of water by weight of the minced skipjack tuna, heating under stirring at 80 to 100° C. for 5 to 30 min, and then lowering the temperature to 50 to 60° C. to obtain a skipjack tuna slurry;
    (2) adding 0.2% to 3.2% of protease by weight of the minced skipjack tuna to the skipjack tuna slurry, carrying out hydrolyzation for 5 to 9 h while keeping the temperature at 50 to 55° C., then heating to 85 to 95° C. which is kept for 15 to 30 min to deactivate the enzyme, and centrifuging to obtain a supernatant, which is a crude enzymatic hydrolysate;
    (3) adding 0.5% to 1.0% of activated charcoal by weight of the crude enzymatic hydrolysate to the crude enzymatic hydrolysate, stirring for 0.5 to 1.0 hour at a temperature of 45 to 55° C., and then filtering through a 0.5 μm filter paper to obtain a refined enzymatic hydrolysate;
    (4) concentrating the refined enzymatic hydrolysate under vaccum and spray-drying to obtain the skipjack tuna extract.

2. The method according to claim 1, characterized in that the protease is one or more of NEUTRASE® (bacterial protease), FLAVOURZYME® (bacterial peptidase), papain, ALCALASE® (bacterial protease) and proteolytic enzymes.

* * * * *